US006063592A

United States Patent [19]
Lee

[11] Patent Number: 6,063,592
[45] Date of Patent: May 16, 2000

[54] KELL PROTEIN PROTEOLYTIC ACTIVITY

[75] Inventor: Soohee Lee, New York, N.Y.

[73] Assignee: New York Blood Center, Inc., New York, N.Y.

[21] Appl. No.: 09/192,048

[22] Filed: Nov. 13, 1998

[51] Int. Cl.[7] .............................. C12P 21/00; C12N 9/48; C12N 9/50
[52] U.S. Cl. ........................ 435/68.1; 435/212; 435/219
[58] Field of Search .................................. 435/68.1, 212, 435/219

[56] References Cited

U.S. PATENT DOCUMENTS

| | | | |
|---|---|---|---|
| 5,462,869 | 10/1995 | Ohwaki et al. | 435/212 |
| 5,468,623 | 11/1995 | Ohwaki et al. | 435/68.1 |
| 5,468,633 | 11/1995 | Ohwaki et al. | 435/212 |
| 5,589,336 | 12/1996 | Lee et al. | 435/6 |
| 5,688,640 | 11/1997 | Yanagisawa | 435/6 |
| 5,804,379 | 9/1998 | Lee et al. | 435/6 |

OTHER PUBLICATIONS

Sohee Lee, "Molecular Basis of Kell Blood Group Phenotypes", Vox. Sang. 1997,73:1–11.
Weiner et al., "Decreased Fetal Erythropoiesis and Hemolysis in Kell Hemolytic Anemia", Am. J. Obstet. Gynecol. 1996, 174: 547–551.
Vaughan et al., "Inhibition of Erythroid Progenitor Cells By Anti–Kell Antibodies In Fetal Alloimmune Anemia," N. Engl. J. Med. 1998, 338:798–803.
Lee et al., "Molecular Cloning and Primary Structure of Kell Blood Group Protein," Proc. Natl. Acad. Sci USA 1991, 88: 6353–6357.
Lee et al., "Organization of the Gene Encoding the Human Kell Blood Group Protein," Blood 1995, 85: 1364–1370.
Lee et al., "The Human Kell Blood Group Gene Mops to Chromosome 7q33 and This Expression is Restricted to Erythroid Cells," Blood 1993 81: 2804–2809.
Lee et al., "Prenatal Diagnosis of Kell Blood Groups Genotypes: KEL 1 and KEL 2," Am. J. Obstet. and Gynecol. 1996, 175: 455–459.
Spence et al., "Prenatal Determination of Genotypes Kell and Cellano in At–Risk Pregnancies," J. Reprod. Med. 1997, 42: 353–357.
Mateo et al. "Highlights On Endothelins: A Review," Pharmacol. Res. 1997, 36: 339–351.
C. Rosendorff, "Endothelin, Vascular Hypertrophy, and Hypertension," Cardiovasc. Drugs and Therapy 1996, 10: 795–802.
McMillan et al., "Endothelin–1 Increases Intracellular Calcium In Human Monocytes and Causes Production of Interleukin–6," Crit. Care Med. 1995, 23: 34–40.
Agui et al., "Stimulation of Interleukin–6 Production by Endothelin In Rat Bone Marrow Derived Stromal Cells," Blood 1994, 84: 2531–2538.

Turner et al. Mammalian Membrane Metallopeptidases: NEP, ECE, KELL and PEX, FASEB.J. 1997, 11: 355–364.
S. Khamlichi et al., "Purification and Partial Characterization of the Erythrocyte Kx Protein Deficient in McLeod Patients," Eur. J. Biochem 1995, 228: 931–934.
Ho et al., "Isolation of the Gene for McLeod Syndrome That Encodes a Novel Membrane Transport Protein," Cell. 1994, 77: 869–880.
Korth et al., "Construction, Expression and Characterization of a Soluble Form of Human Endothelin–Coverting–Enzyme 1," FEBS Lett. 1997, 417: 365–370.
Turner and Murphy, "Molecular Pharmacology of Endothelin Converting Enzymes," Biochemical Pharmacology 1996, 91: 91–102.
Russo et al., "Association of SK and Kell Blood Group Proteins," J. Biol. Chem. 1998, 273(22): 13950–13956.
Givertz et al. "New Targets For Heart–Failure Therapy: Endothelin, Inflammatory Cytokines, and Oxidative Stress," Lancet 1998, 352: SI 34–38.
Saita et al., "Mitogenic Activity of Endothelin on Human Cultured Prostatic Smooth Muscle Cells," European Journal of Pharmacology 1998, 349: 123–128.
M. Stjernquist, "Endothelins–Vasoactive Peptides and Growth Factors," Cell Tissue Res. 1998, 292: 1–9.
Hoang et al., "Novel Activity of Endothelin–Converting Enzyme:Hydrolysis of Bradykinin," Biochem J. 1997, 327: 23–26.
Barnes et al., "Metallopeptidase Inhibitors Induce An Up–Regulation of Endothelin–Converting Enzyme Levels and Its Redistribution From the Plasma Membrane to an Intracellular Compartment," Journal of Cell Science 1996, 109: 919–928.
Turner et al., "Endopeptidase–24.11 (Neprilysin) and Relatives," in *Intracellular Protein Catabolism*, ed. Suzuki and Bond, Plenum Press, New York 1996, pp. 141–148.
Emoto et al., "Endothelin–Converting Enzyme–2 Is a Membrane–bound, Phosphoramidon–Sensitive Metalloprotease With Acidic pH Optimum," J. Biol. Chem. 1995, 270(25): 15262–15268.
Dalyot et al., "Erythropoietin Triggers A Burst of GATA–1 in Normal Human Erythroid Cells Differentiating in Tissue Culture," Nucleic Acid Research 1993, 21: 4031–4037.

(List continued on next page.)

*Primary Examiner*—Robert A. Wax
*Attorney, Agent, or Firm*—Hoffmann & Baron, LLP

[57] ABSTRACT

A method for cleaving polypeptides includes contacting a polypeptide with a recombinant or isolated Kell protein having proteolytic activity for the polypeptide. A method for converting big endothelins-1, -2 and -3 to endothelins-1, -2 and -3 respectively comprises contacting the big endothelin with Kell protein having proteolytic activity for cleaving big endothelin-1, -2 and -3 to endothelin-1, -2 or -3 respectively. In another embodiment, the Kell protein cleaves vasoactive intestinal peptide.

3 Claims, 3 Drawing Sheets

OTHER PUBLICATIONS

Murphy et al. "Generation By the Phosphoramidon–Sensitive Peptidases, Endopeptidase–24.11 and Thermolysin, Of Endothelin–1 and C–Terminal Fragment From Big Endothelin–1," Br. J. Pharmacol. 1994, 113: 137–142.

Abassi et al. "Metabolism of Endothelin–1 and Big Endothelin–1 By Recombinant Neutral Endopeptidase EC. 3.4.24.11," Br. J. Pharmacol. 1993, 109: 1024–1028.

Vijayaraghavan, "The Hydrolysis of Endothelins By Neutral Endopeptidase 24.11 (Endkephalinase)," J. Biol. Chem. 1990, 265: 14150–14155.

"Neprilysis Family (M13)," in Evolutionary Families of Metallopeptidases, pp. 188–189.

MacCumber, "Endothelin in Brain: Receptors, Mitogenesis, and Biosynthesis in Glial Cells," Proc. Natl. Acad. Sci. USA 1990, 87:2359–2363.

SEQUENCE LISTING

<160> NUMBER OF SEQ ID NOS: 27

<210> SEQ ID NO 1
<211> LENGTH: 22
<212> TYPE: DNA
<213> ORGANISM: Homo sapiens

<400> SEQUENCE: 1
aacttccaga actgtggccc tc                                             22

<210> SEQ ID NO 2
<211> LENGTH: 21
<212> TYPE: DNA
<213> ORGANISM: Homo sapiens

<400> SEQUENCE: 2
cagtccctgc agcttcaatg g                                              21

<210> SEQ ID NO 3
<211> LENGTH: 37
<212> TYPE: DNA
<213> ORGANISM: Homo sapiens

<400> SEQUENCE: 3
agcttggatc ccgggcatca tcaccatcat cacaact                             37

<210> SEQ ID NO 4
<211> LENGTH: 29
<212> TYPE: DNA
<213> ORGANISM: Homo sapiens

<400> SEQUENCE: 4
gtgatgatgg tgatgatgcc cgggatcca                                      29

<210> SEQ ID NO 5
<211> LENGTH: 36
<212> TYPE: DNA
<213> ORGANISM: Homo sapiens

<400> SEQUENCE: 5
ggaaggtgtc cccttgggac gttaacgctt actatt                              36

<210> SEQ ID NO 6
<211> LENGTH: 29
<212> TYPE: DNA
<213> ORGANISM: Homo sapiens

<400> SEQUENCE: 6
gcccgtgggc catgatgctg ccagcagcg                                      29

<210> SEQ ID NO 7
<211> LENGTH: 26
<212> TYPE: DNA
<213> ORGANISM: Homo sapiens

<400> SEQUENCE: 7
gctggcagca tcatggccca cgggct                                         26

<210> SEQ ID NO 8
<211> LENGTH: 27
<212> TYPE: DNA
<213> ORGANISM: Homo sapiens

-continued

```
<400> SEQUENCE: 8
taacagcctg ttgctgtatg cctgcag                                27

<210> SEQ ID NO 9
<211> LENGTH: 29
<212> TYPE: DNA
<213> ORGANISM: Homo sapiens

<400> SEQUENCE: 9
tcgcactgga tccaacctac gatgatggt                              29

<210> SEQ ID NO 10
<211> LENGTH: 24
<212> TYPE: DNA
<213> ORGANISM: Homo sapiens

<400> SEQUENCE: 10
ctcaagtcag tacagtgacc ccta                                   24

<210> SEQ ID NO 11
<211> LENGTH: 30
<212> TYPE: DNA
<213> ORGANISM: Homo sapiens

<400> SEQUENCE: 11
gatcaccatc accatcacca tggggatcct                             30

<210> SEQ ID NO 12
<211> LENGTH: 30
<212> TYPE: DNA
<213> ORGANISM: Homo sapiens

<400> SEQUENCE: 12
ctagaggatc cccatggtga tggtgatggt                             30

<210> SEQ ID NO 13
<211> LENGTH: 24
<212> TYPE: DNA
<213> ORGANISM: Homo sapiens

<400> SEQUENCE: 13
tcttggctct ctccgcttcg tcct                                   24

<210> SEQ ID NO 14
<211> LENGTH: 24
<212> TYPE: DNA
<213> ORGANISM: Homo sapiens

<400> SEQUENCE: 14
tcttggctct ctccgcttcg tcct                                   24

<210> SEQ ID NO 15
<211> LENGTH: 38
<212> TYPE: PRT
<213> ORGANISM: Homo sapiens

<400> SEQUENCE: 15

Cys Ser Cys Ser Ser Leu Met Asp Lys Glu Cys Val Tyr Phe Cys His
 1               5                  10                  15

Leu Asp Ile Ile Trp Val Asn Thr Pro Glu His Val Val Pro Tyr Gly
            20                  25                  30
```

Leu Gly Ser Pro Arg Ser
         35

<210> SEQ ID NO 16
<211> LENGTH: 17
<212> TYPE: PRT
<213> ORGANISM: Homo sapiens

<400> SEQUENCE: 16

Ser Ser Ser Leu Met Asp Lys Glu Val Tyr Phe His Leu Asp Ile Ile
 1               5                  10                  15

Trp

<210> SEQ ID NO 17
<211> LENGTH: 17
<212> TYPE: PRT
<213> ORGANISM: Homo sapiens

<400> SEQUENCE: 17

Val Asn Thr Pro Glu His Val Val Pro Tyr Gly Leu Gly Ser Pro Arg
 1               5                  10                  15

Ser

<210> SEQ ID NO 18
<211> LENGTH: 38
<212> TYPE: PRT
<213> ORGANISM: Homo sapiens

<400> SEQUENCE: 18

Cys Ser Cys Ser Ser Leu Met Asp Lys Glu Cys Val Tyr Phe Cys His
 1               5                  10                  15

Leu Asp Ile Ile Trp Val Asn Thr Pro Glu His Val Val Pro Tyr Gly
             20                  25                  30

Leu Gly Ser Pro Arg Ser
         35

<210> SEQ ID NO 19
<211> LENGTH: 37
<212> TYPE: PRT
<213> ORGANISM: Homo sapiens

<400> SEQUENCE: 19

Cys Ser Cys Ser Ser Trp Leu Asp Lys Glu Cys Val Tyr Phe Cys His
 1               5                  10                  15

Leu Asp Ile Ile Trp Val Asn Thr Pro Glu Gln Thr Ala Pro Tyr Gly
             20                  25                  30

Glu Gly Asn Pro Pro
         35

<210> SEQ ID NO 20
<211> LENGTH: 41
<212> TYPE: PRT
<213> ORGANISM: Homo sapiens

<400> SEQUENCE: 20

Cys Thr Cys Phe Thr Tyr Lys Asp Lys Glu Cys Val Tyr Tyr Cys His
 1               5                  10                  15

Leu Asp Ile Ile Trp Val Asn Thr Pro Glu Gln Thr Val Pro Tyr Gly
             20                  25                  30

Leu Ser Asn Tyr Arg Gly Ser Phe Arg
         35                  40

```
<210> SEQ ID NO 21
<211> LENGTH: 28
<212> TYPE: PRT
<213> ORGANISM: Homo sapiens

<400> SEQUENCE: 21

His Ser Asp Ala Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 22
<211> LENGTH: 20
<212> TYPE: PRT
<213> ORGANISM: Homo sapiens

<400> SEQUENCE: 22

His Ser Asp Ala Val Phe Thr Asp Asn Tyr Thr Arg Leu Arg Lys Gln
 1               5                  10                  15

Met Ala Val Lys
            20

<210> SEQ ID NO 23
<211> LENGTH: 8
<212> TYPE: PRT
<213> ORGANISM: Homo sapiens

<400> SEQUENCE: 23

Lys Tyr Leu Asn Ser Ile Leu Asn
 1               5

<210> SEQ ID NO 24
<211> LENGTH: 14
<212> TYPE: PRT
<213> ORGANISM: Homo sapiens

<400> SEQUENCE: 24

His Ser Asp Ala Val Phe Thr Asp Asn Tyr Thr Arg Leu Arg
 1               5                  10

<210> SEQ ID NO 25
<211> LENGTH: 14
<212> TYPE: PRT
<213> ORGANISM: Homo sapiens

<400> SEQUENCE: 25

Lys Gln Met Ala Val Lys Lys Tyr Leu Asn Ser Ile Leu Asn
 1               5                  10

<210> SEQ ID NO 26
<211> LENGTH: 7
<212> TYPE: PRT
<213> ORGANISM: Homo sapiens

<400> SEQUENCE: 26

Tyr Leu Asn Ser Ile Leu Asn
 1               5

<210> SEQ ID NO 27
<211> LENGTH: 13
<212> TYPE: PRT
<213> ORGANISM: Homo sapiens
```

```
<400> SEQUENCE: 27

His Ser Asp Ala Val Phe Thr Asp Asn Tyr Thr Arg Leu
 1               5                  10
```

KELL PROTEIN PROTEOLYTIC ACTIVITY

The invention relates to protein cleavage by Kell protein. Kell protein is involved in the processing and cleavage of bioactive peptides. The bioactivity includes vasoconstriction, vasodilation, cell differentiation and cell proliferation. The Kell proteins are also involved in the suppression of erythropoiesis in fetuses and newborns of mothers sensitized to Kell antibodies.

BACKGROUND OF THE INVENTION

The Kell blood group is one of the major antigenic systems in human red cells. It is complex and currently 23 alloantigens are determined to be present on, or associated with Kell protein. S. Lee, "Molecular Basis of Kell Blood Group Phenotypes", *Vox Sang.* 1997, 73:1–11, provides a summary of the Kell blood group system and of the molecular basis for the different phenotypes.

Among the various Kell alloantigens, KEL1 (K) is the strongest immunogen and antibodies to KEL1 cause severe reactions when mismatched blood is transfused. Sensitization to KEL1, although most common because of mismatched blood transfusion, can also occur during incompatible pregnancies. About 0.1% of pregnant mothers have antibodies to KEL1. This is a medical problem since babies who have inherited KEL1 from the father, are at risk of hemolytic disease of the newborn (HDN) if the mothers have Kell antibodies. HDN, caused by Kell-related antibodies, is unlike that caused by anti-Rh(D). Anti-Rh(D) causes red cell hemolysis while Kell antibodies are thought to suppress erythropoiesis (Weiner, et al., "Decreased Fetal Erythropoiesis and Hemolysis in Kell Hemolytic Anemia", *Am. J Obstet. Gynecol.* 1996, 174:547–551). Unlike anti-Rh(D) there is little correlation between anti-Kell titers, bilirubin levels and the severity of HDN, and anemic babies do not have a corresponding reticulocytosis. An in vitro study which supports these clinical observations has been recently reported by Vaughan et al., "Inhibition of Erythroid Progenitor Cells by Anti-Kell Antibodies in Fetal Alloimmune Anemia", *N. Engl. J. Med.* 1998, 338:798–803. Vaughen et al. concluded that both monoclonal and naturally occurring anti-Kell antibodies inhibit the growth of Kell-positive erythroid progenitor cells grown from mononuclear cells. The inhibition was dependent on the dose of the antibodies. These findings suggest that suppression of erythropoiesis at the progenitor-cell level is an important mechanism of fetal anemia due to anti-Kell antibodies. The mechanisms by which Kell antibodies suppress erythropoiesis are not known.

The Kell cDNA has been cloned (Lee et al, "Molecular Cloning and Primary Structure of Kell Blood Group Protein", *Proc. Natl. Acad. Sci. U.S.A.* 1991, 88:6353–6357) and characterization has also been done of the organizations of the 19 exons of the KEL gene (Lee et al., "Organization of the Gene Encoding the Human Kell Blood Group Protein", *Blood* 1995, 85:1364–1370; Lee et al., "The Human Kell Blood Group Gene Maps to Chromosome 7q33 and This Expression is Restricted to Erythroid Cells", *Blood* 1993, 81:2804–2809).

Methods were designed to genotype fetal KEL1 (Lee et al., "Prenatal Diagnosis of Kell Blood Group Genotypes: KEL1 and KEL2", *Am. J. Obstet. and Gynecol.,* 1996, 175:455–459. This prenatal diagnostic procedure is currently used commercially to genotype fetus at risk for hemolytic disease of the newborn (HDN). Spence et al, "Prenatal Determination of Genotypes Kell and Cellano in At-Risk Pregnancies", *J. Reprod. Med.* 1997, 42:353–357.

Women (KEL:-1,2) who have antibodies to KEL1 and have KEL1/2 partners have a 50% chance of carrying a KEL:1 baby who is at risk of fetal anemia. A diagnostic method for the differential determination of Kell genotype in a patient is described in U.S. Pat. No. 5,589,336 to Lee and Redman.

Endothelins are known to have a variety of biological activities such as vasoconstriction, vasodilation, cell proliferation and cell migration. (Mateo and de Artinano, "Highlights On Endothelins: A Review", *Pharmacol. Rev.* 1997, 36:339–351; C. Rosendorff, "Endothelin, Vascular Hypertrophy, And Hypertension", *Cardiovasc. Drugs* 1997, 10:795–802. Endothelins also have regulatory effects on certain cytokines such as IL-6 which is known to be one of many growth factors affecting hematopoiesis. McMillan et al., "Endothelin-1 Increases Intracellular Calcium In Human Monocytes And Causes Production of Interleukin-6", *Crit. Care Med.* 1995, 23:34–40; Agui et al., "Stimulation of Interleukin-6 Production By Endothelin In Rat Marrow-Derived Stromal Cells", *Blood* 1994, 84:2531–2538.

KEL gene products exhibit strong homology with neutral endopeptidase-24.11 (NEP) which is the prototype of a family of zinc metalloproteinases that also includes the endothelin-converting enzymes (ECE) and the product of the PEX gene, and which are also structurally related to the bacterial enzymes thermolysin and lactococcol endopeptidase. Turner and Tanzawa, "Mammalian Membrane Metallopeptidases: NEP, ECE, KELL and PEX" *FASEB J.* 1997, 11:355–364. Biologically active substrates for NEP includes enkephalins and the atrial natriuretic peptide family. ECE catalyzes the final step in the biosynthesis of the vasoconstrictor peptide, endothelin (ET). However, according to these authors, no enzymatic activity has yet been attributed to KELL proteins and they remain peptidases in search of a substrate.

SUMMARY OF THE INVENTION

The invention includes a method of proteolysis by Kell proteins. Specific proteolytic methods include converting big endothelin (-1, -2, and -3) respectively to endothelin (-1, -2 and -3) by contacting the big endothelin with Kell protein having proteolytic activity for cleaving big endothelin to endothelin. In another aspect of the invention, vasoactive intestinal peptide is cleaved by contacting with Kell protein having proteolytic activity for vasoactive intestinal peptide.

The cleaved proteins are involved in vasocontriction and vasodilation. Therefore, the invention can be used in the development of therapeutic agents and screening assays. Moreover, the proteolytic function of the Kell proteins can be utilized in the management and study of hypertension, and cell differentiation and proliferation such as in hematopoiesis and developmental process. These discoveries relate to ongoing studies by the inventors herein into the mechanisms of suppression of erythropoiesis observed in fetuses and newborns from mothers who are previously sensitized to Kell antibodies.

DETAILED DESCRIPTION OF THE INVENTION

Figure 1:
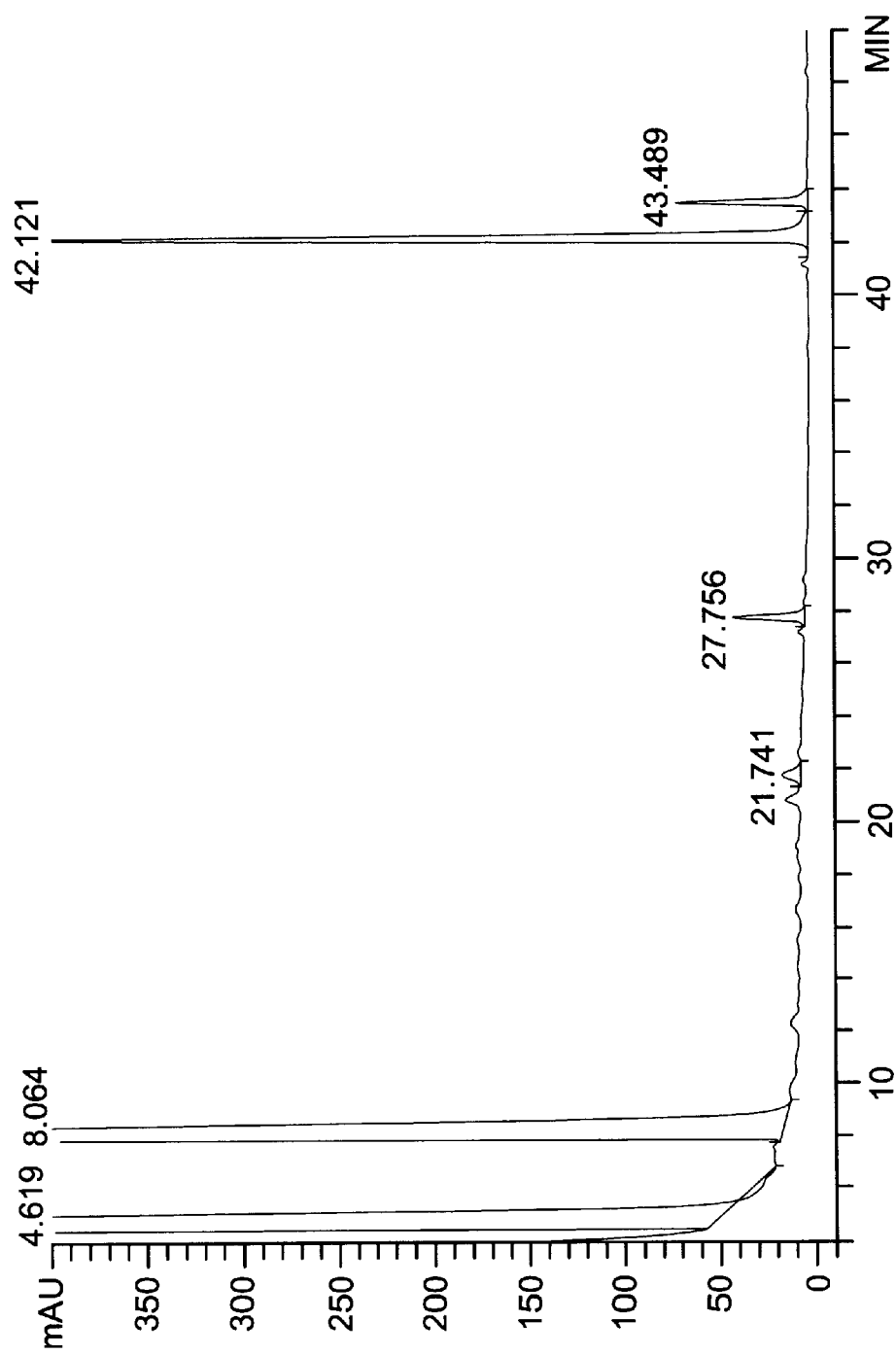
FIG. 1 is a graph illustrating HPLC after contacting big endothelin with soluble recombinant Kell proteins.

Human Kell blood group proteins share a pentameric consensus sequence HEXXH with a large family of zinc-dependent endopeptidases. Kell has its closest homology with neutral endopeptidase 24.11 (also called NEP-24.11 or CD-10), endothelin converting enzyme (ECE-1) and the PEX gene product that as a group comprise the M13 subfamily of mammalian zinc dependent endopeptidases. The M13 family has a variety of proteolytic activity, but the proteolytic activity of Kell has not been known. CD10 has broad substrate specificity and cleaves a number of biopeptides yielding active or inactive forms. ECE-1 is more specific and its principal function is to process big endothelin (38 amino acids) to yield the potent vasoconstrictor endothelin-1 by cleavage of the $Trp^{21}$–$Val^{22}$ bond. ECE-1 also hydrolyzes the vasodilator bradykinin. PEX protein degrades parathyroid hormone derived peptides.

Kell, CD-10 (NEP-24.11), ECE-1 and the product of the PEX gene are all type II membrane glycoproteins with structural and sequence homologies. Amino acid sequence identity is particularly high in the C-terminal domain. Within this C-terminal region, Kell has 34–36% amino acid homology with the rest of the M13 family protease. Ten cysteine residues are conserved in the M13 family protease which predicts similarities in 3-D structure. Kell differs from the proteases in the subfamily in that it is covalently linked to XK (S. Khamlichi et al., *Eur. J. Biochem.* 1995, 220:931–934; M. Ho et al., *Cell* 1994, 77:869–880) which has the physical characteristics of a membrane transporter but whose function is unknown.

It has now been found that Kell protein is able to specifically cleave certain proteins. In particular, Kell protein is able to generate endothelins from their inactive precursor forms and cleave vasoactive intestinal peptide at multiple sites. We expressed a secreted form of wild-type Kell protein in sf9 cells by placing the cDNA that encodes the extracellular portion of Kell in a baculovirus transfer vector pAcGP67-A. As a control, an inactive mutant Kell protein was expressed that contained glycine instead of the mandatory glutamic acid in the putative active site (H ELLH→HGLLH, mutant). A secreted form of Js$^a$ Kell phenotype (L597P) was also expressed. Wild-type and Js$^a$ Kell proteins did not cleave a large number of small synthetic chromogenic peptides, including those hydrolyzed by CD-10. As determined by N-terminal amino acid sequencing and mass spectrometry of the cleaved products, wild-type Kell and Js$^a$ Kell, but not the control protein, cleaved big-endothelin-1, big-endothelin-2 and big-endothelin-3 respectively yielding endothelin-1, endothelin-2 and endothelin-3 at the $trp^{21}$–$val^{22}$ bond. Wild-type and Js$^a$ Kell proteins also cleaved vasoactive intestinal peptide (VIP), a vasodilator, at multiple sites. Enzymatic activity was inhibited by phosphoramidon, an agent which selectively inhibits thermolysin and the M13 family of mammalian zinc endopeptidases. The data demonstrate that Kell is a proteolytic enzyme and is believed to function, for example, in the regulation of vascular tone.

Kell differs from the endothelin converting enzymes ECE-1 and-2 that are known activators of endothelins, in affinity for the different big endothelins and in other enzymatic parameters:

(1) Kell protein cleaves big-endothelin -1,-2 and -3 with substrate affinities of approximately 80 μM (measured by HPLC), approximately 20 μM (measured by HPLC) and <2 μM (approximately) (measured by EIA), respectively. The Kell protein does not cleave bradykinin which is cleaved by ECE-1. Km values for ECE-1, 2 and 3 are in reverse order.

(2) The pH optimum of Kell protease is 6.0–6.5 and it is believed to work intracellularly as well as an ectoenzyme bound to plasma membrane. Soluble ECE-1 preferentially cleaves big-endothelin-1 and has a pH optimum of 6.6–6.8 (Korth et al., *FEBS Lett* 1997, 417:365–370).

(3) Concentration of Zn metalloprotease inhibitor, Phosphoramidon which gives 50% of inhibition is 50–100 μM. Phosphoramidon is a fungal metabolite which inhibits certain zinc peptidases. A. J. Turner and L. J. Murphy, *Biochemical Pharmacology* 1996, 91:91–102.

A unique characteristic of Kell protein structure which differs from other members of the M13 family is Kell complexation with Xk protein linked through a disulfide bond. In addition, a unique characteristic of the Kell gene promoter is that KEL has two GATA-1, and AP-1 binding sites and one CACCC box between nt. −1 to −185. Erythropoietin, which is one of the growth factors needed in red cell production, up regulates GATA-1 expression which may regulate Kell expression. Increased Kell may increase ET-3 release. ET-3 also up regulates ET-1. Thus, erythropoietin treatment can lead to hypertension. In addition, Jsa (KEL6) phenotype is more prevalent in blacks which may be linked to clinical observation of increased hypertension in blacks. The enzyme parameters of Jsa phenotype for big endothelins may be different resulting in hypertension in blacks. Furthermore, Kell or soluble Kell may be used to develop Kell specific inhibitors for preferential management of ET3, ET2 and ET1.

The endothelins are a family of three, 21 amino acid, bioactive peptides that play important roles in the regulation of vascular tone and in the development of the cardiovascular and enteric nervous systems. The three endothelins are encoded by separate genes and are initially synthesized as large inactive precursors called pre-pro-endothelins (212, 178 and 238 amino acids respectively for pre-pro-endothelin-1,-2 and -3). The pre-pro-endothelins are cleaved at pairs of basic amino acids to yield intermediate, inactive proteins named big-endothelin-1 (big ET-1), big-endothelin-2 (big ET-2) and big-endothelin-3 (big ET-3). The big-endothelins are finally converted by endothelin converting enzymes (ECE) to the bioactive endothelins (ET-1, -2 and -3). Big-ET-1 and -2 are cleaved at a $Trp^{21}$–$Val^{22}$ bond and big-ET-3 at Trp-Ile to produce the 21-residue active peptides. ET-1, -2 and -3 act on 2 distinct G-protein-coupled receptors ($ET_A$ and $ET_B$) with different affinites and the 3 endothelins share, but also differ, in their biological effects. C.. Rosendorff, *Cardiovasc. Drugs* 1997, 10:795–802.

Using a hematopoiesis cell culture system grown on methyl cellulose plates, our preliminary studies also showed that a low concentration of phosphoramidon (3.5–7.0 µM) increased cell growth, while higher concentration (50–100 µM) inhibited cell growth. Meanwhile, the concentration of phosphoramidon needed to inhibit the proteolytic cleavage of big-endothelins by ECE-1 and Kell protein are different. While it is not intended to be bound by theory, it is possible that Kell participates in the proteolytic processing of growth factors or cytokines during hematopoiesis.

We studied the protease activity of soluble Kell proteins and a native form (membrane bound complexed with and without XK) both recombinant. We purified soluble Kell as an immunocomplex with biotinylated anti-K14 bound to streptavidan beads and showed that soluble Kell bound to immuno complex did cleave big endothelin-1. It is believed that the Kell on red cells will also behave the same.

METHODS
Construction of Expression Vectors of Secreted Forms of Kell Protein

Soluble Wild Type Kell

The area of nt 322–620 of Kell cDNA was amplified using the forward (5'-AACTTCCAGAACTGTGGCCCTC-3' (SEQ ID NO:1)) and reverse primers(5'-CAGTCCCTGCAGCTTCAATGG-3' (SEQ ID NO:2)) by PCR. The PCR product was ligated to SmaI site of vaculo virus transfer vector pAcGP67A. The resulting plasmid was cut with EcoRI to which (pAcGP67A containing Kell cDNA fragment of nt 322–528) 1923 bp EcoRI cut fragment of Kell cDNA (nt 528–2450) was ligated.

Soluble Wild Type Kell With Cys72Ser Substitution and His Tag at N-Terminus

Following two forward and reverse oligonucleotides are used to create HindIII overhang, BstXI overhang, BamHI site and six Histidine tag at N-terminus of Kell protein with Cys72Ser. The Kell expression construct in pRc/CMV described by D. Russo et al., *Journal of Biological Chemistry* 1998, 273(22): 13950–13956 which has Cys72Ser substitution was cut with HindIII and BstXI. The forward 37 mer and reverse 29 mer oligonucleotides were annealed and ligated to the HindIII and BstXI cut Kell expression construct in pRc/CMV which has Cys72Ser substitution and has been previously described by Russo et al., Id.

KHDBmHXF:
(SEQ ID NO:3)
5'-*AGCT*TGGATC CCGGGCATCA TCACCATCAT CAC*AACT*-3'
   HindIII BamHI       His His  His His His  His BstXI KHDBm:HXF:
(SEQ ID NO:4)
5'-GTGATGATGGTGATGATGCC CGGGATCCA-3'
                                  BamHI  HindIII The restriction enzyme overhangs are underlined and italicized. The restriction enzyme sites inserted are underlined. The six histidine coding sequences are in bold. The resulting plasmid was cut with BamHI and StuI (Kell nt 1406) and the 1.2 kb insert was replaced the wild type Kell placed in vaculo virus transfer vector, pAc GP67A at BamHI site.

Soluble Kell With E582G Substitution (Mutant)

Following two sets of primers were used to insert A865G mutation in two sets of PCRs. All the resulting construct made by PCR was sequenced and any errors were corrected by replacing the portion with correct piece using convenience enzyme sites.

PCR1:
Forward primer,
(SEQ ID NO:5)
HpaF:5'-GGAAGGTGTCCCCTTGGGAC<u>GTTAAC</u>GCTTACTATT-3'
                                       HpaF Reverse primer, GLR:
(SEQ ID NO:6)
5'-GC<u>C</u>CGTGGGC CATGATGCTG CCAGCAGCG-3'

PCR2:
Forward primer, GLF:
(SEQ ID NO:7)
5'-GCTGGCAGCA TCATGGCCCA CG<u>G</u>GCT-3'

Reverse primer, NheR:
(SEQ ID NO:8)
5'-TAACAGCCTG TTGCTGTATG CCTGCAG-3'

156 bp product from PCR1 and 248 bp product from PCR2 were purified in 0.8% low melting agarose gel electrophorosis and combined in a PCR to join the two PCR products yielding 376 bp PCR product which contained the A1865G mutation. This 376 bp product was cut with HpaI (nt 1735) and NheI (nt 2043) and the resulting 309 bp DNA was inserted at HpaI and NheI sites of Kell cDNA in transfer vector which has C1737T and T1740C mutations to create a unique HpaI site at nt 1735. The 638 bp fragment between StuI (1406) and NheI (2043) site of Kel cDNA in sKell in pAc GP67A construct was replaced with the 638 bp respective fragment with A1865G mutation in a transfer vector cut with StuI and NheI.

Soluble Kell With E582G Substitution and 6 Histidine Tag at N-Terminus (Mutant)

The 638 bp fragment between StuI (1406) and NheI (2043) site of Kell cDNA in sKell in pAc GP67A construct with 6 Histidine tag at N-terminus was replaced with the 638 bp respective fragment with A1865G mutation in a pAc GP67A vector cut with StuI and NheI.

Soluble KEL6 (Js$^a$)

Total RNA was prepared from peripheral blood of a person with KEL6,-7 phenotype. Total RNA was reverse transcribed using oligo dT and RT-PCR was performed using Forward primer, 322F (nt Kell 322) and Reverse primer NheR. The 1.7 Kb PCR product was subcloned in pT7 blue® vector. The 638 bp fragment between StuI (1406) and NheI (2043) site of Kell cDNA in sKell in pAc GP67A construct was replaced with the 638 bp respective fragment with T1910C mutation in pT7 blue® vector cut with StuI and NheI. The area cut with StuI and NheI of sKell with 6 histidine tag in pAc GP67A was replaced with the same 638 bp fragment with T1910C mutation to generate the sKEL6 with 6 His tag at N-terminus.

Soluble CD10

Human CD10 cDNA in vector (M. A. Shipp et al., *Proc. Natl. Acad. Sci. U.S.A.* 1988, 85:4819–4823) and the following primers were used to amplify the extracellular portion of the cDNA.

Forward primer, caBamF:5'-TCGCACTGGA TCCAAC-CTAC GATGATGGT-3' (SEQ ID NO:9)

Reverse primer, Ca2373R:5'-CTCAAGTCAG TACAGT-GACC CCTA -3' (SEQ ID NO:10)

The PCR product of 2.2 kb was cut with BamHI and AvrII and ligated at BamHI and XbaI site of pAc GP67A and subcloned.

To place the 6 Histidine tag at N-terminus in the pAcGP67A vector, the following two oligonucleotides which are complimentary with each other and contained BamHI enzyme site, BglII and XbaI overhangs and 6 histidine coding sequences were annealed and ligated to the BamHI and XbaI cut pAcGP67A vector.

BgH6BmXF:

(SEQ ID NO:11)
5'-<u>GAT CACCATC ACCATCACCA TGGGGATCCT</u>-3
    BglII                         BamHI

BgH6BmXF:

(SEQ ID NO:11)
5'-<u>GAT CACCATC ACCATCACCA TGGGGATCCT</u>-3
    BglII                         BamHI

BgH6BmXR:

(SEQ ID NO:12)
5'-<u>CTAG</u>AGGATC CCCATGGTGA TGGTGATGGT-3'
  XBaI    BamHI

The 2.2 Kb BamHI and Not I cut insert from sCD10 in pAcGP67A was ligated to bamHI and NotI cut (His)6 pAcGP67A vector.

Soluble ECE

Following primers were used to amplify the extracellular portion of the ECE cDNA using bone marrow library cDNA in lambda gt10 DNA as template DNA Forward primer, ECEF2:5'-TCTTGGCTCT CTCCGCT-TCG TCCT-3' (SEQ ID NO:13)

Reverse prime, ECER:5'-TCTTGGCTCT CTCCGCTTCG TCCT-3' (SEQ ID NO:14) 2069 bp PCR product was subcloned at SmaI site of pAcGP67A vector. BamHI and NotI cut insert was ligated to (His)6 pAcGP67A vector to place 6 Histidine tag at N-terminus. Two ligation steps followed by subcloning were employed. First, 1273 bp BamHI cut fragment (nt 1519) was ligated at BamHI site of the (His)6 pAcGP67A vector and the resulting plasmid was cut with PflMI (nt 1020) and Not I to which 1331 bp BamHI and NotI cut insert prepared from sECE/pAcGP67A was ligated to complete the construct.

Transfection, Preparation of High-Titer Viral Stocks and Express of Recombinant Proteins 1.3 μg of recombinant vector carrying respective cDNA in 100 μl of Grace Basic media was co-transfected with 0.17 μg of BaculoGold (Pharmingen) to 9×10$^5$ sf9 cells in 35 mm plate using 5 μl of Cellfectin (Gibco BRL) mixed with 100 μl of Grace basic media as DNA carrier according to the Company protocol provided by Gibco BRL.

High titer viral stocks were prepared following basically the company protocol provided by Pharmingen. Briefly, the transfected virus containing media was harvested on 5th day from transfection by centrifugation at 2000 g for 5 mins. The transfection virus stock was amplified 2 times using end point dilution methods in which 1,10 and 100 ul of transfection virus stock was used to infect the 0.5×10$^5$ sf9 cells in 1 ml of Grace media in 12 well plate. First amplified virus stock ranging from 2–8×10$^7$ MOI (multiplication of infection) per ml (from 10 μl of transfection viral stock added well) was used to prepare high titer viral stock by infecting the f9 cells monolayered in excell 400 media with approximately 0.9 MOI of the viral stock.

Recombinant protein was expressed by infecting monolayered sf9 cells in excell 400 and 420 1:1 mixed media (serum protein free media) with approximately 10 MOI of the high titer viral stock. The media containing recombinant protein was collected by centrifugation of the media at 2000 g for 5 mins to remove cell debris and 40,000 g for 25 mins to remove virus particles. The media containing the protein was stored at −70° C.

Digestion of Big Endothelin-1,-2, and -3 (Big ET-1, -2, and -3) With Soluble Recombinant Proteins 1) For HPLC Analysis Enzyme reaction mixture was made by mixing 8–16 μl of 1 mg/ml big ET-1 (1-38), big ET-2 (1-37 or 1-38) and big ET-3 (1-41) (American Peptide Co., Sunnyvale, Calif. and Sigma, St. Louis, Mo. and Peptide Institute, Inc., Osaka, Japan), 10 μl 1 mM $ZnCl_2$ final concentration 86 μM and 70 μl recombinant protein containing media. The mixture was incubated at 37° C. for different time periods. Twenty to 25 aliquots of this incubation mix was assayed by reverse HPLC. The conditions of the analysis were:

Solvent A: 0.1% TFA/2,5% 1-Propanol (PrOH)/$H_2O$ (500 μl

Trifluoroacetic acid+1 L $H_2O$+25 ml 1-PrOH).

Solvent B; 0.09% TFA/2.5% 1-PrOH/90% Acetonitrile/$H_2O$ (450 μl

TFA+1 L Acetonitrile+100 ml $H_2O$+25 ml 1-PrOH).

Gradient condition was 1–61% A In B over 0–60 minutes at a flow rate of 0.15 ml/min. The column used was reverse phase C18 column (2×150 mm, Vydac).

2) For EIA Assay

Enzyme reaction mix was made by mixing various amounts of 10 μM big ET's, 20 μl of 10 Kell assay buffer (0.5 M HEPES, 0.5 mM $ZnCl_2$ and 1.5 NaCl containing 4% (v/v) of supernatant boiled BSA) and various amounts of soluble protein containing media (ranging from 0.0313 μl to 4 μl) and $H_2O$ to make a total volume of 200 μl. The enzyme reaction was incubated at 37° C. for 15 min. At the end of the incubation time, 100 μl of 5 mM EDTA was added to terminate the reaction. Various amounts of the sample up to 100 μl were used in Enzyme-linked Immunoassay using Endothelin-1EIA kit (Cayman Chemical).

The results are shown in FIG. 1: results by HPLC analysis. Results are also summarized in Table 1:

TABLE 1

Big Endothelin-1(1-38) Cleaved by Recombinant Soluble Kell Protein

| MW by Mass Spect. | Amino Acid Sequences | Peaks at Retention Time |
|---|---|---|
| 4282 Da | CSCSSLMDKECVYFCHLDII-WVNTPEHVVPYGLGSPRS(1–38) (SEQ ID NO: 15) | 42.121 |
| 2491 Da | -S-SSLMDKE-VYF-HLDII(W)(1–21) (SEQ ID NO: 16) | 43.489 |
| 1811 Da | Cys not derivatized and not detected VNTPEHVVPYGLG(S)PR(S)(22–38) (SEQ ID NO: 17) | 27.756 |

The results also showed that (1) Kell protein cleaves big-endothelin -1, -2 and -3 with substrate affinities of approximately 80 μM (measured by HPLC), approximatelt 20 μM (measured by HPLC) and <2

μM (approximately) (measured by EIA), respectively. The Kell protein does not cleave bradykinin which is cleaved by ECE-1. Km values for ECE-1, 2 and 3 are in reverse order. (2) The pH optimum of Kell protease is 6.0–6.5 and it is believed to work intracellularly as well as an ectoenzyme bound to plasma membrane.

more than wild type Kell. Further investigation will be done to ascertain whether the cutting is due to some other protease secreted by the cell upon infection of baculovirus containing Kell cDNA's. Results are summarized in Table 2 and FIG. 2.

TABLE 2

Vasoactive Intestinal Peptide (VIP, 1–28) Cleaved By SF9 Cell Media Infected With Baculovirus Containing Recombinant Soluble Kell (Jsa) cDNA

| MW by Mass Spect. | Amino Acid Sequences | Peaks at Retention Time |
| --- | --- | --- |
| 3325 Da | HSDAVFTDNYTRLRKQMAVKKYLNSILN(1–28) (SEQ ID NO: 21) | 36.631 |
| 2382 Da | HSDAVFTDNYTRLRKQMAVK(1–20) (SEQ ID NO: 22) | 28.839 |
| 964.14 Da | KYLNSILN(21–28) (SEQ ID NO: 23) | 29.775 |
| 1695.5 Da | HSDAVFTDNYTRLR(1–14) (SEQ ID NO: 24) | 26.867 |
| 1649.5 Da | KQMAVKKYLNSILN(15–28) (SEQ ID NO: 25) | 34.585 |
| 834.98 Da | YLNSILN(22–28) (SEQ ID NO: 26) | 29.775 |
| 1540 Da | HSDAVFTDNYTRL(1–13) (SEQ ID NO: 27) | 30.404 |

(3) Concentration of Zn metalloprotease inhibitor, Phosphoramidon which gives 50% of inhibition is approximately 50–100 μM.

Kell Proteins Used in Cutting Big ET- 1,-2,-3

We used recombinant soluble form of Kell protein to cleave big ET's. We also used recombinant native form of Kell alone and bound to XK to show that it also cuts big-ET's. The results were the same with soluble and bound form. Purified soluble Kell (isolated as biologically pure) as an immunocomplex with biotinylated anti-K14 bound to streptavidan beads also cleaved big ET. It can be predicted that Kell proteins on the cell membrane such as on red cells will cleave big ET's in the same fashion. One significance of the cutting is that the kinetics of cutting by Kell are different than the ones by known ECE's. Peptide Sequences of Big Endothelin-1,-2 and -3 and Cleavage Sites Which Produce Endothelin-1, -2 and -3 (1–21):

```
Big Endothelin-1(1-38)
                                        (SEQ ID NO:18)
                        ↓
CSCSSLMDKECVYFCHLDIIW²¹V²²NTPEHVVPYGLGSPRS Big Endothelin-2(1-37)
                                        (SEQ ID NO:9)
                        ↓
CSCSSWLDKECVYFCHLDIIW²¹V²²NTPEQTAPYGEGNPP Big Endothelin-3(1-41)
                                        (SEQ ID NO:20)
                        ↓
CTCFTYKDKECVYYCHLDIIW²¹V²²NTPEQTVPYGLSNYRGSFR
```

VIP Cutting by sKell Proteins

Figure 2:
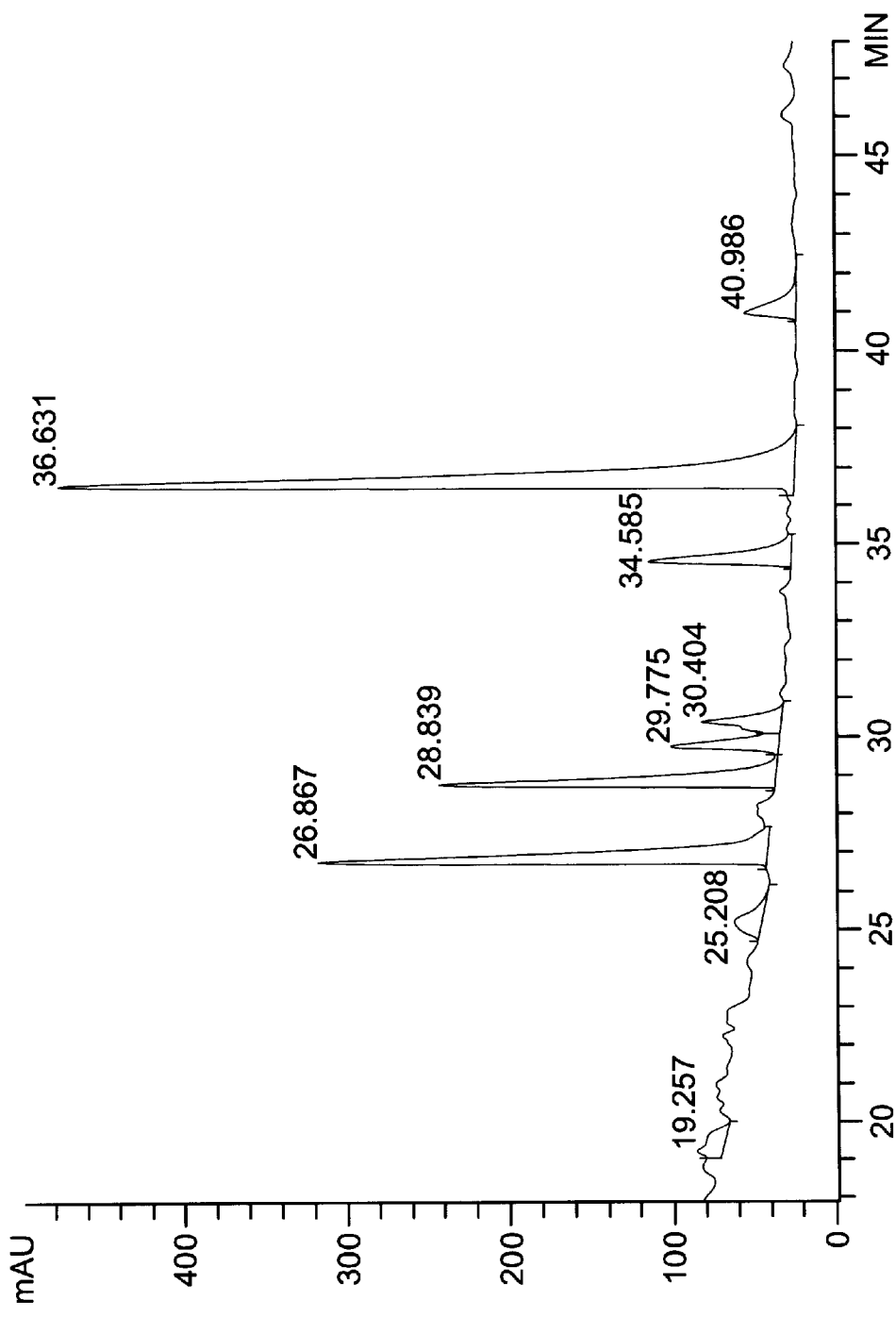
FIG. 2 is a graph illustrating HPLC after contacting VIP with soluble recombinant Kell proteins.

Soluble Kell proteins (sKell) proteins were used to cut vasoactive intestinal peptide (VIP). As shown in FIG. 2, Kell cleaves VIP. The results show that the sf9 protein free media containing sKell (wild type and Jsa) cleaves VIP more when compared to the media containing mutant Kell. Jsa cleaves Expression of Kell protein in tissues other than erythroid tissue were observed. This leads us to hypothesize that Kell will be shown to have an important role (such as cell proliferation) in tissues such as brain and testes, etc.

Soluble Recombinant Protein Expressed in SF9 Insect Cell Media

Figure 3:
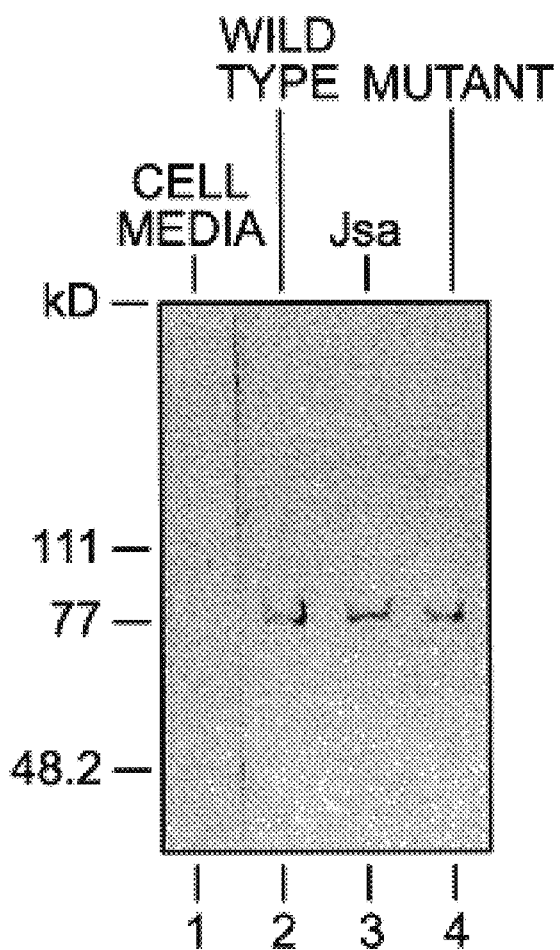
FIG. 3 is an SDS PAGE illustrating Kell proteins.

FIG. 3 shows immunoblotting of Soluble Kells (sKells) secreted into cell culture media. Each 5 ul aliquots of sample media per lane were subjected to 7.5% SDS PAGE and analyzed by immunoblotting using polyclonal anti-Kell. The extracellular portion of Kell protein the recombinant proteins are expressed.

Lanes are as Follows: 1, cell culture media; 2, wild type Kell; 3, KEL6 (Jsa); 4, Kell with E582G substitution (mutant).

While there have been described what are presently believed to be preferred embodiments of the invention, those skilled in the art will recognize that other and further embodiments can be made without departing from the spirit of the invention, and it is intended to include all such further modifications and changes as come within the true scope of the claims set forth herein.

I claim:

1. A method of cleaving Big Endothelin-1, -2, or -3 or vasoactive intestinal peptide comprising contacting Big Endothelin-1, -2, or -3 or vasoactive intestinal peptide with recombinant or isolated Kell proteins having proteolytic activity for cleaving Big Endothelin-1, -2. or -3 or vasoactive intestinal peptide.

2. A method of converting big endothelin to endothelin comprising contacting big endothelin-1, -2 or -3 with recombinant or isolated Kell proteins having proteolytic activity for cleaving big endothelin-1, –2 or -3 to endothelin-1, -2 or -3 respectively.

3. A method of cleaving vasoactive intestinal peptide comprising contacting the vasoactive intestinal peptide with recombinant or isolated Kell proteins having proteolytic activity for cleaving vasoactive peptide.

* * * * *